US012697240B2

(12) United States Patent
Shepherd et al.

(10) Patent No.: US 12,697,240 B2
(45) Date of Patent: Aug. 4, 2026

(54) MODULAR SUPPORT SYSTEM

(71) Applicant: ORTHO INNOVATIONS, LLC, Selbyville, DE (US)

(72) Inventors: Bryan Shepherd, Selbyville, DE (US); Eugene Welch, Ellicott City, MD (US); Morris Brian Polsky, Reisterstown, MD (US); Edward Spirko, Millsboro, DE (US)

(73) Assignee: Ortho Innovations, LLC, Selbyville, DE (US)

( * ) Notice: Subject to any disclaimer, the term of this patent is extended or adjusted under 35 U.S.C. 154(b) by 462 days.

(21) Appl. No.: 18/106,364

(22) Filed: Feb. 6, 2023

(65) Prior Publication Data

US 2023/0172739 A1     Jun. 8, 2023

Related U.S. Application Data

(63) Continuation-in-part of application No. 17/987,361, filed on Nov. 15, 2022, which is a continuation of application No. 16/533,127, filed on Aug. 6, 2019, now Pat. No. 11,771,577.

(51) Int. Cl.
A61F 5/01 (2006.01)
A47C 20/02 (2006.01)
A61F 5/058 (2006.01)

(52) U.S. Cl.
CPC .......... A61F 5/0106 (2013.01); *A47C 20/021* (2013.01); *A61F 2005/0167* (2013.01); *A61F 5/0585* (2013.01)

(58) Field of Classification Search
CPC .... A61F 5/0106; A61F 5/0585; A61F 5/0111; A61F 5/013; A61F 5/0127; A61F 5/0113; A61F 2005/0167; A61F 13/061; A61F 13/062; A61F 13/065; A61F 13/066; A47C 20/021; A43B 7/141; A43B 7/142; A43B 7/143; A43B 17/14; A43B 17/16
USPC .............. 602/16, 26, 27, 65; 128/882; 36/44
See application file for complete search history.

(56) References Cited

U.S. PATENT DOCUMENTS

| | | | | |
|---|---|---|---|---|
| 3,604,023 A | * | 9/1971 | Lynch | A61B 6/0442 |
| | | | | D6/601 |
| 4,041,940 A | | 8/1977 | Frankel | |
| 4,697,583 A | * | 10/1987 | Mason | A61F 5/0123 |
| | | | | 602/26 |
| 4,765,318 A | * | 8/1988 | Tranberg | A61F 5/0109 |
| | | | | 602/26 |
| 4,889,109 A | | 12/1989 | Gifford | |

(Continued)

*Primary Examiner* — Alireza Nia
*Assistant Examiner* — Michael Milo
(74) *Attorney, Agent, or Firm* — Dickinson Wright PLLC

(57) ABSTRACT

A modular knee brace assembly includes a brace and a wedge. The brace comprises a sleeve portion comprising a first opening at a first end of the sleeve portion and a second opening at a second end of the sleeve portion, the first opening and the second opening adapted to enable a first portion of a user's body to pass through the sleeve portion and a second portion of the user's body to remain within the sleeve portion and a first mating unit comprising a plurality of discrete attachment points coupled to an outer surface of the sleeve portion. The wedge comprises a second mating unit, wherein the second mating unit is adapted to couple with a set of the plurality of discrete attachment points to support one or more portions of the user's body.

20 Claims, 9 Drawing Sheets

(56)         References Cited

U.S. PATENT DOCUMENTS

| | | | | |
|---|---|---|---|---|
| 4,910,818 | A | * | 3/1990 | Grabill ................. A47C 20/021 |
| | | | | 5/494 |
| 5,125,123 | A | * | 6/1992 | Engle ................... A47C 20/025 |
| | | | | 128/845 |
| 5,216,771 | A | * | 6/1993 | Hoff ..................... A47C 20/025 |
| | | | | 5/652 |
| 5,418,991 | A | | 5/1995 | Shiflett |
| 6,640,368 | B2 | | 11/2003 | Roston |
| 6,935,697 | B2 | | 8/2005 | Conion |
| D646,790 | S | | 10/2011 | Castillo |
| 2002/0022108 | A1 | * | 2/2002 | Krantz ............... A44B 18/0057 |
| | | | | 428/100 |
| 2006/0030803 | A1 | * | 2/2006 | Nordt, III .............. A41D 13/08 |
| | | | | 602/26 |
| 2007/0185423 | A1 | | 8/2007 | Brown |
| 2012/0284901 | A1 | * | 11/2012 | Webb ................... A41D 13/065 |
| | | | | 2/227 |
| 2017/0197818 | A1 | | 7/2017 | Berreklouw |
| 2017/0360586 | A1 | * | 12/2017 | Dempers ............... A61F 5/0109 |
| 2021/0267320 | A1 | * | 9/2021 | Yamashita ......... A44B 18/0065 |

* cited by examiner

MODULAR SUPPORT SYSTEM

CROSS-REFERENCE TO RELATED APPLICATIONS

This application is a continuation-in-part of U.S. patent application Ser. No. 17/987,361, filed on Nov. 11, 2022, which is a continuation of U.S. patent application Ser. No. 16/533,127, filed on Aug. 6, 2019, the entire disclosures of which are incorporated herein by reference.

BACKGROUND

This section provides background information related to the technology associated with the present disclosure and, as such, is not necessarily prior art.

The disclosure and prior art relates to knee brace devices and more particularly pertains to a new knee brace device for supporting a knee in a plurality of sleeping positions.

SUMMARY

An embodiment of the disclosure meets the needs presented above by generally comprising a brace that is worn around a knee after orthopedic surgery has been performed on the knee. A wedge is removably coupled to the brace when the brace is worn around the knee. The wedge is positioned on a back side of the knee to support the knee in a bent position when the user is lying on the user's back. An inner knee support is removably coupled to the brace when the brace is worn around the knee. The inner knee support extends between each of the user's knees when the user lies on their side. An outer knee support is removably coupled to the brace when the brace is worn around the knee. In this way the outer knee support supports the knee when the user lies on the user's side.

There has thus been outlined, rather broadly, the more important features of the disclosure in order that the detailed description thereof that follows may be better understood, and in order that the present contribution to the art may be better appreciated.

There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DETAILED DESCRIPTION

Figure 1:
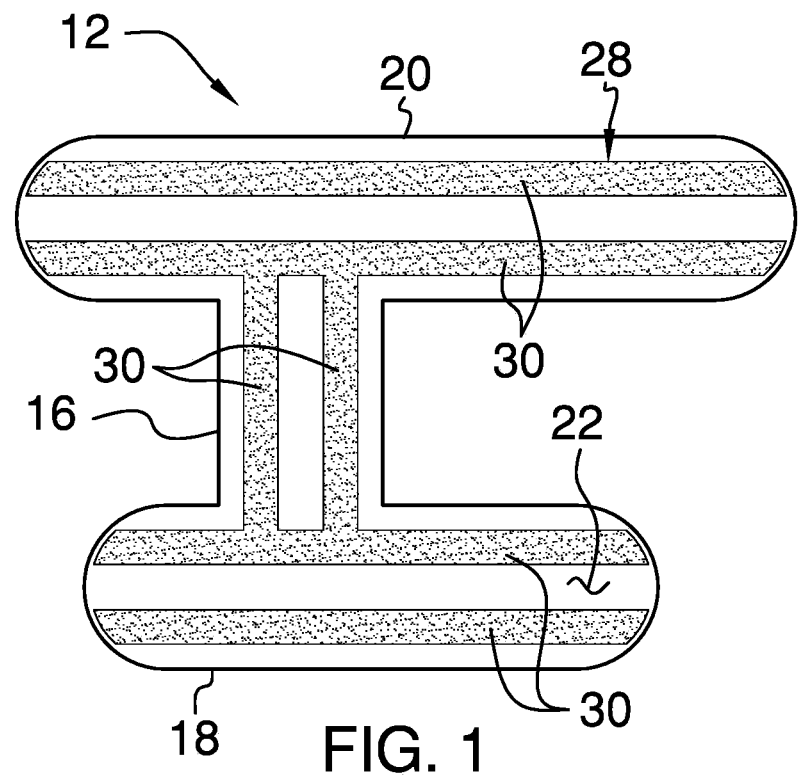
FIG. 1 is a top view of a brace of a modular knee brace assembly according to an embodiment of the disclosure.
Figure 2:
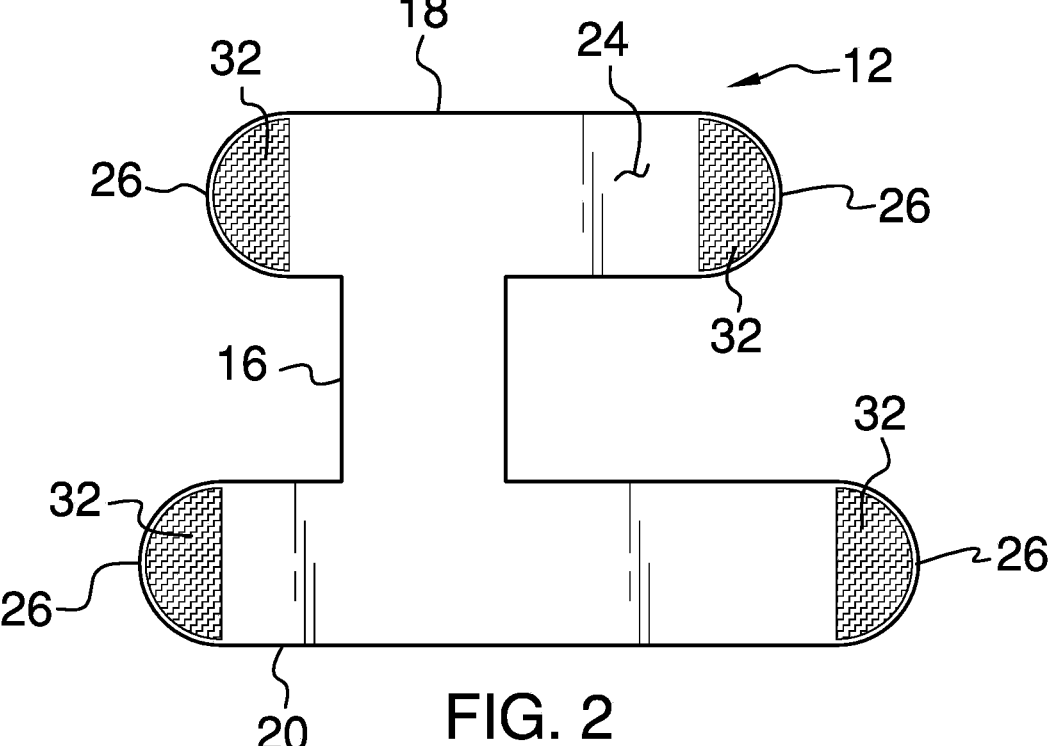
FIG. 2 is a bottom view of a brace of an embodiment of the disclosure.

With reference now to the drawings, and in particular to FIGS. 1 through 8 thereof, a new knee brace device embodying the principles and concepts of an embodiment of the disclosure and generally designated by the reference numeral 10 will be described.

As best illustrated in FIGS. 1 through 8, the modular knee brace assembly 10 generally comprises a brace 12 that is worn around a knee 14 after orthopedic surgery has been performed on the knee 14. The brace 12 comprises a first panel 16 extending between a second panel 18 and a third panel 20. The first panel 16 is oriented at a right angle with each of the second 18 and third 20 panels such that the brace 12 has an I shape. Additionally, the first panel 16 extends along an axis that is offset from a lateral centerline of each of the second 18 and third 20 panels. The second panel 18 has a length that is shorter than a length of the third panel 20.

Each of the first 16, second 18 and third 20 panels has a top surface 22 and a bottom surface 24, and each of the second 18 and third 20 panels has a pair of distal ends 26 with respect to the first panel 16. The bottom surface 24 is wrapped around the knee 14 having the top surface 22 being exposed. The second panel 18 is wrapped around the user's upper calf, the third panel 20 is wrapped around the user's lower thigh and the first panel 16 extends vertically along a back of the user's knee 14.

A first mating unit 28 is coupled to the brace 12 and the first mating unit 28 is exposed when the brace 12 is worn around the knee 14. The first mating unit 28 comprises a plurality of sets of strips 30. Each of the sets of strips 30 is positioned on the top surface 22 of a respective one of the first 16, second 18 and third 20 panels Moreover, each of the sets of strips 30 is coextensive with the respective first 16, second 18 and third 20 panels. The set of strips 30 on the first panel 16 intersects the set of strips 30 on each of the second 18 and third 20 panels.

A plurality of mating members 32 is each coupled to the brace 12. Each of the mating members 32 releasably engages the first mating unit 28 when the brace 12 is wrapped around the knee 14 for retaining the brace 12 around the knee 14. Each of the mating members 32 is positioned on the bottom surface 24 of a respective one of the second 18 and third 20 panels. Additionally, each of the mating members 32 is aligned with a respective one of the distal ends 26 of the respective second 18 and third 20 panels. Each of the mating members 32 releasably engages the set of strips 30 on the respective second 18 and third 20 panels. Each of the mating members 32 and each of the strips 30 may comprise hook and loop fasteners or the like.

A wedge 34 is removably coupled to the brace 12 when the brace 12 is worn around the knee 14. The wedge 34 is positioned on a back side of the knee 14 to support the knee 14 in a bent position when the user is lying on the user's back. The wedge 34 has a basal surface 36 extending between a pair of top surfaces 38, and the top surfaces 38 are oriented at an angle with each other. Each of the top surfaces 38 abuts the top surface 22 of a respective one of the second 18 and third 20 panels when the brace 12 is worn on the knee 14. A peak 40 of the top surfaces 38 is aligned with aback of the knee 14 thereby supporting the knee 14 in a bent position. The basal surface 36 abuts a support surface 42 upon which the user is lying thereby supporting the knee 14 in the bent position. The wedge 34 may be comprised of a resiliently compressible material for enhancing comfort for the user.

A second mating unit 44 is coupled to the wedge 34 and the second mating unit 44 releasably engages the first mating unit 28 to retain the wedge 34 on the brace. The second mating unit 44 comprises a set of strips 46 that is positioned on each of the top surfaces 38 of the wedge 34. The set of strips 46 of the second mating unit 44 is coextensive with each of the top surfaces 38 of the wedge 34. Moreover, each of the strips 46 of the second mating unit 44 releasably engages respective ones of the strips 30 of the first mating unit 28. Each of the strips 46 of the second mating unit 44 may comprise hook and loop fasteners or the like.

An inner knee support 48 is removably coupled to the brace 12 when the brace 12 is worn around the knee 14. The inner knee support 48 extends between each of the user's knees 14 when the user lies on their side. Moreover, the inner knee support 48 is positioned on an interior side of the knee 14 to support the knee 14 when the user lies on their side opposite of the knee 14 on which the brace 12 is worn. The inner knee support 48 has a first lateral surface 50 and a second lateral surface 52. Each of the first 50 and second 52 lateral surfaces is concavely arcuate with respect to each other to conform to the curvature of a respective one of the user's knees 14 when the user lies on the user's side. The inner knee support 48 is positioned on the user's thigh above the knee 14. The inner knee support 48 may be comprised of a resiliently compressible material for enhancing comfort for the user.

A pair of third mating units 54 is each coupled to the inner knee support 48. Respective ones of the third mating units 54 releasably engage the first mating unit 28 to retain the inner knee support 48 on the brace 12. Each of the third mating units 54 comprises a set of strips 56 and each of the strips 56 of each of the third mating units 54 is positioned on a respective one of the first 50 and second 52 lateral surfaces of the inner knee support 48. Each of the strips 56 on a respective one of the first 50 or second 52 lateral surfaces releasably engages respective ones of the strips 30 of the first mating unit 28. Additionally, each of the strips 56 of the third mating units 54 may comprise a hook and loop fastener or the like.

An outer knee support 58 is removably coupled to the brace 12 when the brace 12 is worn around the knee 14 to support the knee 14 when the user lies on the user's side. The outer knee support 58 is positioned on an outer side of the knee 14 to support the knee 14 when the user lies on the outer side of the knee 14. The outer knee support 58 has a first surface 60 that is concavely arcuate with respect to a second surface 62 such that the first surface 60 can conform to the curvature of the knee 14. The second surface 62 abuts the support surface 42 when the user lies on the user's side. The outer knee support 58 may be comprised of a resiliently compressible material to enhance comfort for the user.

A fourth mating unit 64 is coupled to the outer knee support 58. The fourth mating unit 64 releasably engages the first mating unit 28 to retain the outer knee support 58 on the brace 12. The fourth mating unit 64 comprising a set of strips 66 and each of the strips 66 of the fourth mating unit 64 is positioned on the first surface 60 of the outer knee support 58. Each of the strips 66 of the fourth mating unit 64 releasably engages respective ones of the strips 30 of the first mating unit 28. Additionally, each of the strips 66 of the fourth mating unit 64 may comprise a hook and loop fastener or the like.

Figure 6:
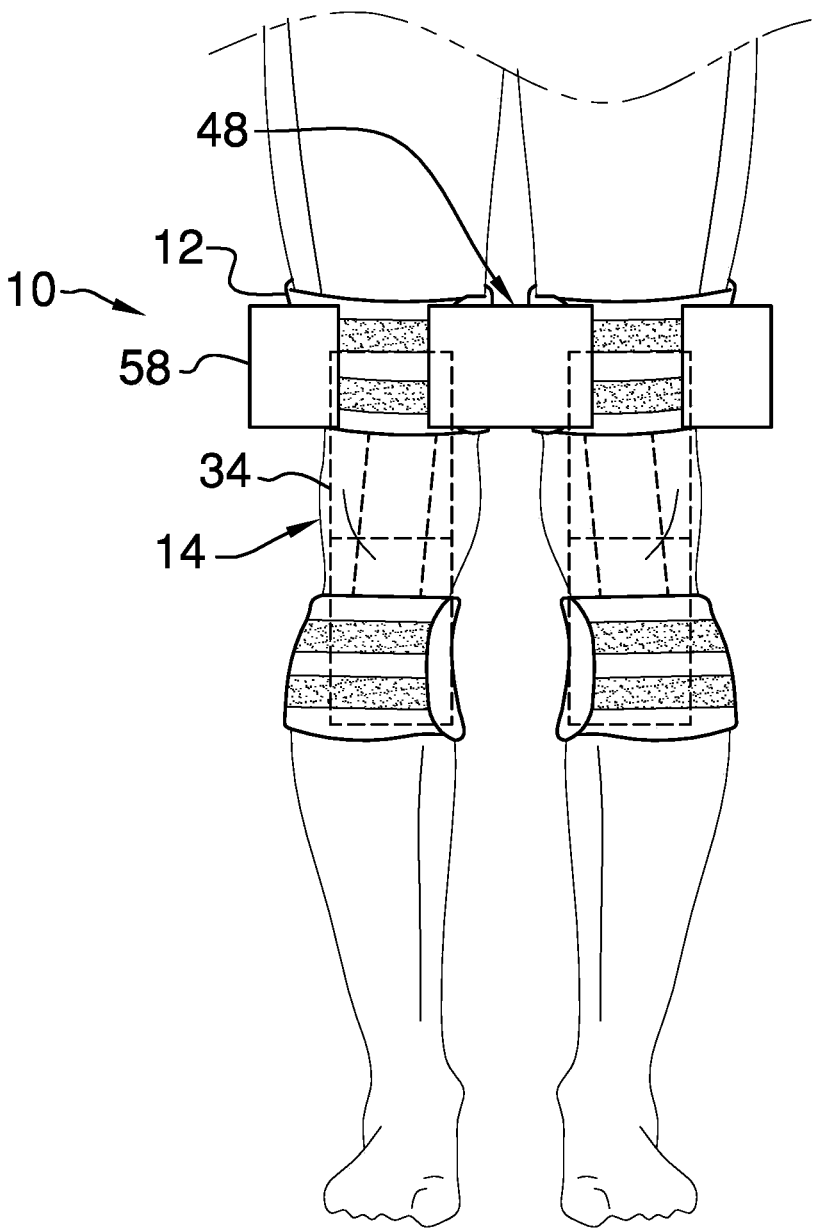
FIG. 6 is a front in-use view of an embodiment of the disclosure.
Figure 7:
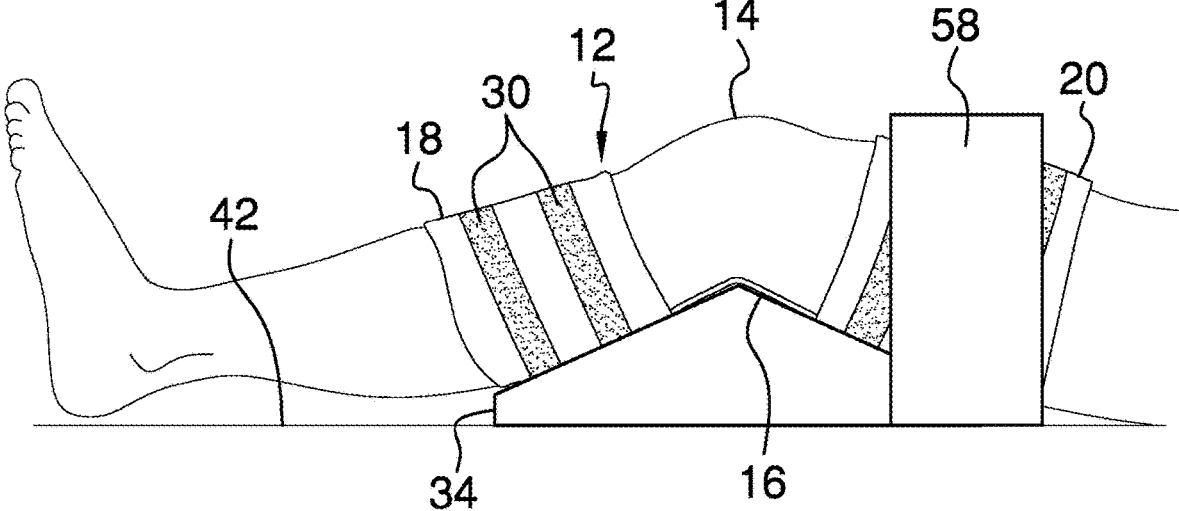
FIG. 7 is a perspective in-use view of an embodiment of the disclosure.
Figure 8:
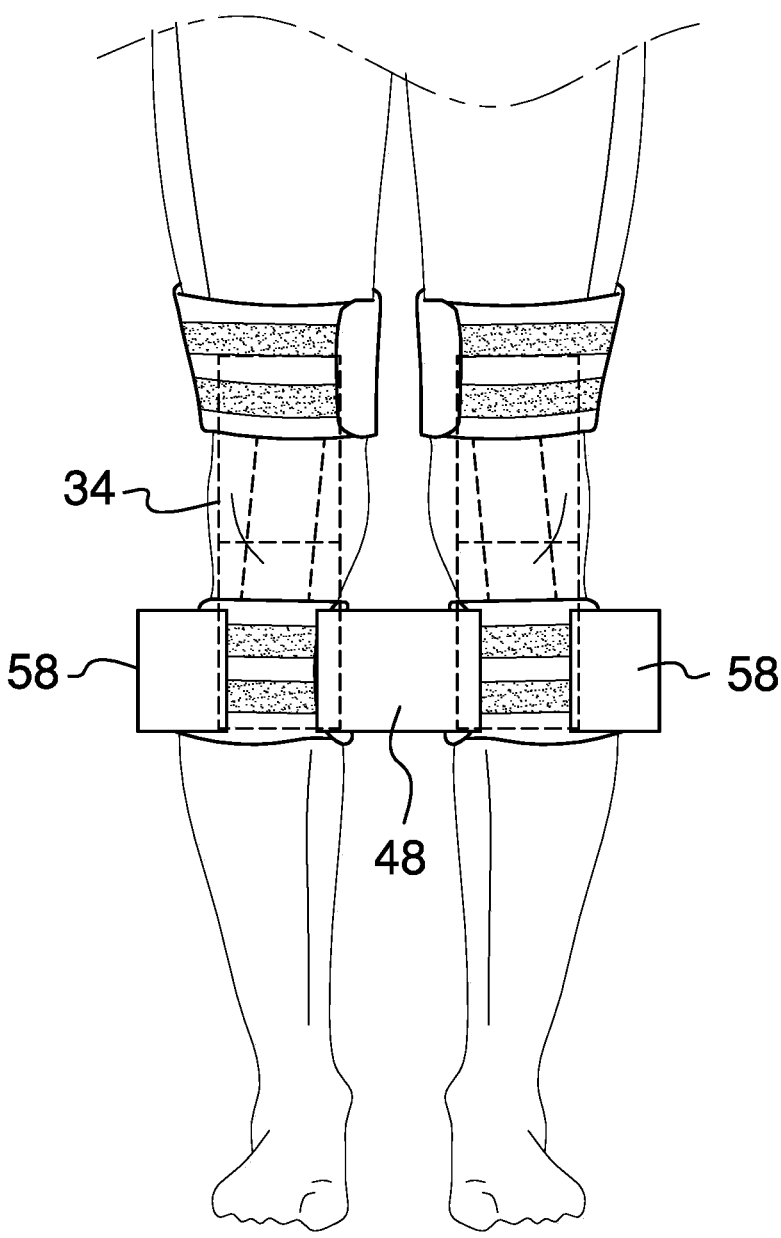
FIG. 8 is a front perspective in-use view of an embodiment of the disclosure.

As is most clearly shown in FIG. 6, a pair of the braces 12 may each be worn around a respective one of the user's knees 14. The inner knee support 48 can be coupled between each of the braces 12. Additionally, a pair of the outer knee supports 58 may each be coupled to a respective one of the braces 12. In this way each of the knees 14 are supported regardless of which side the user is lying on. A pair of the wedges 34 may each be coupled to a respective one of the braces 12 to support each of the knees 14 when the user is lying on their back. As is most clearly shown in FIG. 8, the inner knee support 48 and the outer knee support 58 can be aligned with each of the user's knees.

In use, the brace 12 is worn around the user's knee 14. The wedge 34 is coupled to the brace 12 and the wedge 34 is positioned on the back side of the knee 14. The inner knee support 48 is coupled to the brace 12 and the inner knee support 48 is positioned on the interior side of the knee 14. The outer knee support 58 is coupled to the brace 12 and the outer knee support 58 is positioned on the outer side of the knee 14 support. In this way the user's knee 14 is supported regardless if the user is sleeping on their back, their right side or their left side. Moreover, the brace 12, the wedge 34, the inner knee support 48 and the outer knee support 58 reduce pain during sleeping and enhance the healing process.

Figure 9:
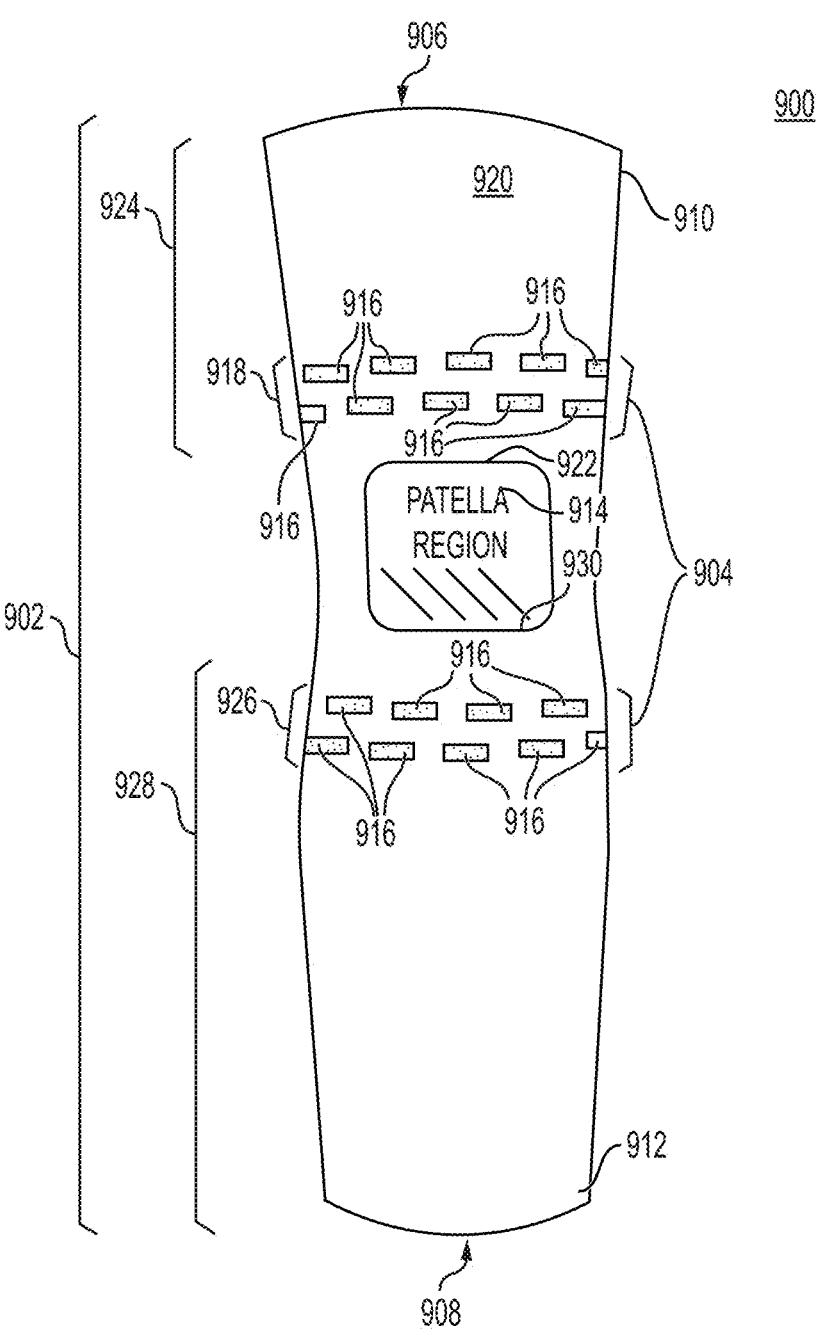
FIG. 9 is a front perspective view of another brace of an embodiment of the disclosure.
Figure 10:
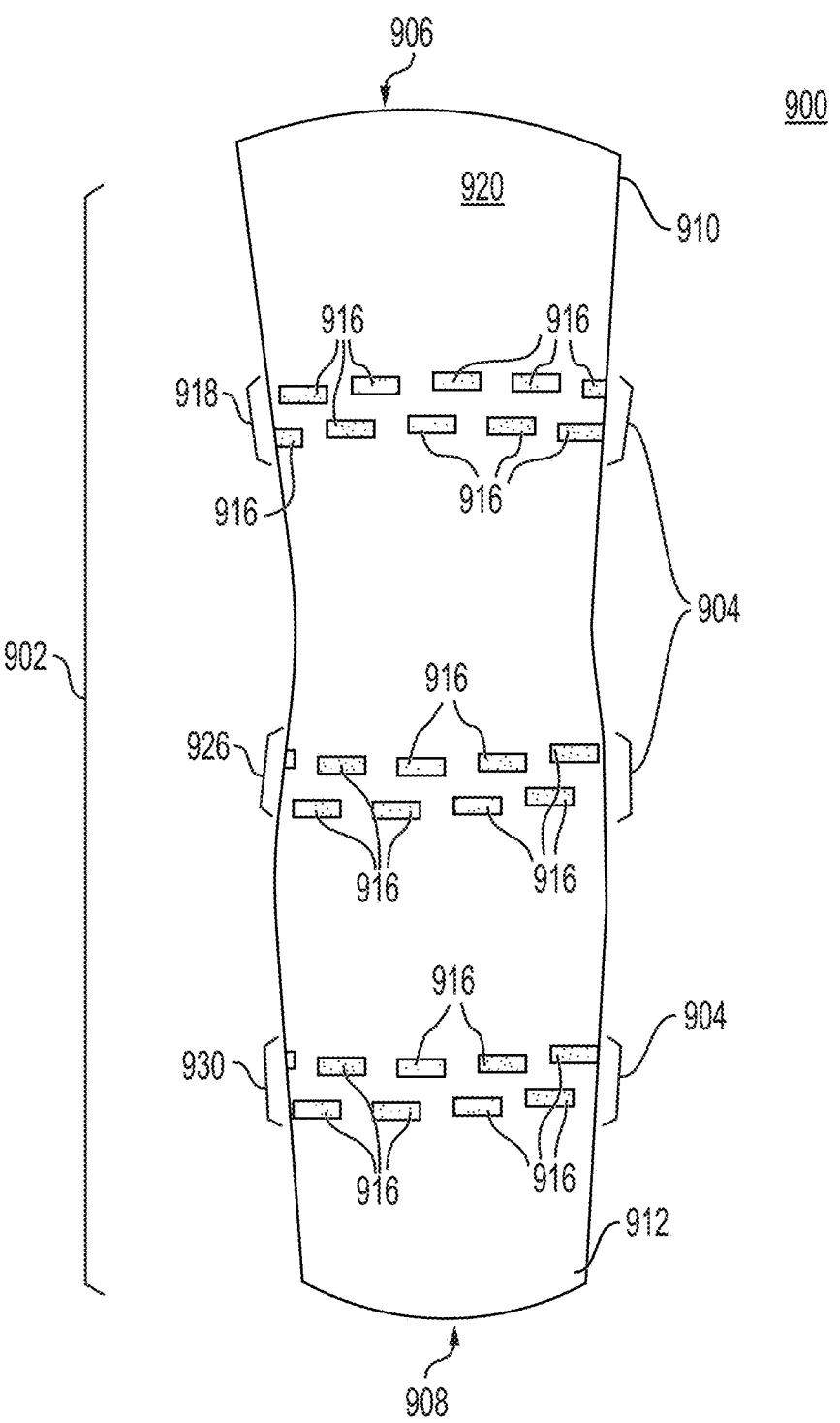
FIG. 10 is a back perspective view of the other brace of an embodiment of the disclosure.

FIGS. 9 and 10 illustrate different perspective views of an exemplary embodiment of a brace that can used with the modular knee brace assembly 10 (referred to as a modular support system hereafter) represented in FIGS. 1-8. FIG. 9 provides a front view of a brace 900, and FIG. 10 provides a back perspective view of the brace 900, in accordance with embodiments described herein.

As shown in FIGS. 9 and 10, the brace 900 includes the following parts: a sleeve portion 902 and a mating unit 904. In FIGS. 9 and 10, the sleeve portion 902 comprises a first opening 906 at a first end 910 of the sleeve portion 902 and a second opening 908 at a second end 912 of the sleeve portion 902. The first opening 906 and the second opening 908 may be adapted to enable a first portion of a user's body (e.g., a lower leg of the user) to pass through the sleeve portion 902 and a second portion of the user's body (e.g., a knee, an upper leg of a user, etc.) to remain within the sleeve portion 902. Also shown in FIG. 9, the sleeve portion 902 further includes a joint region 914 where a user's joint (e.g., knee, elbow, etc.) is located when the brace 900 is worn by the user. In some embodiments, the joint region 914 may be an opening which exposes at least a portion of a joint. As depicted in FIGS. 9 and 10, the sleeve portion 902 assumes a substantially tubular shape. However, in other embodiments, the sleeve portion 902 may assume any shape (e.g., a square or any other desired shape).

As further shown in FIGS. 9 and 10, the mating unit 904 comprises a plurality of discrete attachment points 916 coupled to an outer surface 920 of the sleeve portion 902, where the outer surface 920 is opposite an inner surface (not pictured in FIGS. 9 & 10) which is adjacent to a user's body when the sleeve portion 902 is worn by the user. In FIGS. 9 and 10, and in accordance with embodiments disclosed herein, the plurality of discrete attachment points 916 are arranged in a plurality of rows along a circumference of the sleeve portion 902. Further, in some embodiments, the plurality of discrete attachment points 916 may be substantially evenly spaced about the circumference of the outer surface 920 of the sleeve portion 902. Still yet, in some embodiments, each discrete attachment point in a row of discrete attachment points may be substantially aligned with a corresponding discrete attachment point in an adjacent row of discrete attachment points. Alternatively, in some embodiments, each discrete attachment point in a row of discrete attachment points may be substantially staggered from one or more discrete attachment points in an adjacent row of discrete attachment points. In some embodiments, the plurality of discrete attachment points 916 may be substantially shaped as: a circle, an oval, a triangle, a square, a rectangle, a hexagon, an octagon, a decagon, a semi-hexagon, a semi-octagon, a semi-decagon, or any combination thereof.

In accordance with embodiments described herein, the plurality of discrete attachment points 916 may be coupled to the sleeve portion 902 in one or more sections of the sleeve portion 902. For example, in FIG. 9, a first set 918 of the plurality of discrete attachment points 916 is coupled to a section 924 of the sleeve portion 902, which is adjacent a side 922 of the joint region 914, and a second set 926 of the plurality of discrete attachment points 916 is coupled to a section 928 of the sleeve portion 902, which is adjacent a side 930 of the joint region 914, where the side 930 is opposite the side 922. As another example, as shown in FIG. 10, a third set 930 of the plurality of discrete attachment points 916 is coupled to a section of the sleeve portion 902 near the second end 912 of the sleeve portion 902.

Figures 3, 4, 5:
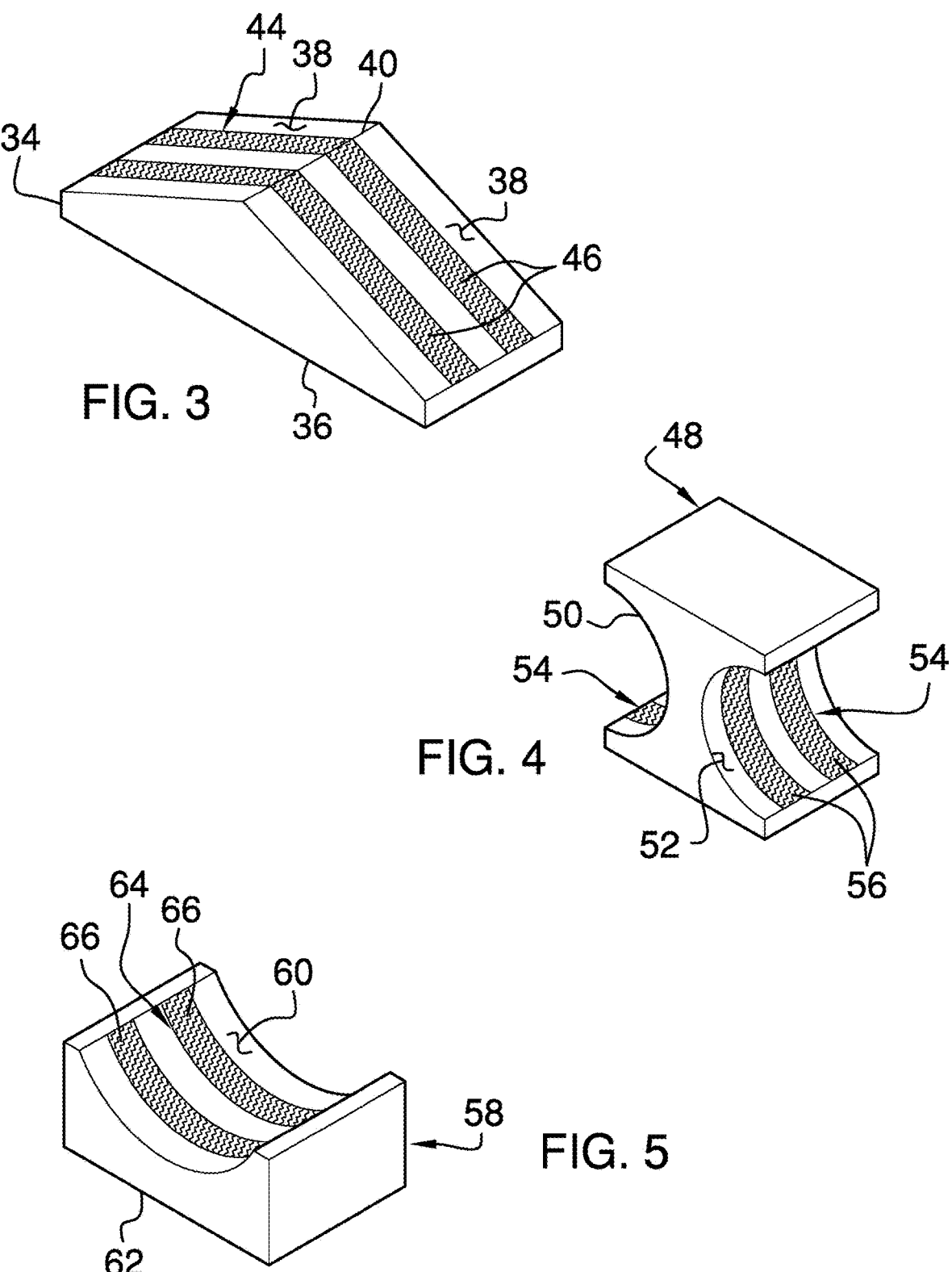
FIG. 3 is a top perspective view of a wedge of an embodiment of the disclosure.
FIG. 4 is a front perspective view of an inner knee support of an embodiment of the disclosure.
FIG. 5 is a perspective view of an outer knee support of an embodiment of the disclosure.

In accordance with embodiments described herein, the sleeve portion 902 may be removably coupled to the inner knee support 48 in FIG. 4 (also referred to herein as the inner support). For example, one or more segments of the third mating units 54 coupled to the first lateral surface 50 in FIG. 4 may be releasably engaged with a set of the plurality of discrete attachment points 916 of the mating unit 904 to retain the inner knee support 48 on the sleeve portion 902 such that the inner support 48 is positioned on a portion of a user's body at a medial side of a joint. Alternatively, or in addition to, one or more segments of the third mating units 54 coupled to the second lateral surface 52 in FIG. 4 may be releasably engaged with a set of a plurality of discrete attachment points of a mating unit of a sleeve portion of a second brace to retain the inner knee support 48 on the sleeve portion of the second brace such that the inner support 48 is positioned on a portion of a user's body at a medial side of a second joint.

In accordance with embodiments described herein, the sleeve portion 902 may be removably coupled to the outer knee support 58 in FIG. 5 (also referred to herein as the outer support). For example, one or more segments of the fourth mating units 64 coupled to the first surface 60 in FIG. 5 may be releasably engaged with a set of the plurality of discrete attachment points 916 of the mating unit 904 to retain the outer support 58 on the sleeve portion 902 such that the outer support 58 is positioned on a portion of a user's body at a lateral side of a joint.

Further, in accordance with embodiments described herein, the sleeve portion 902 may be removably coupled to the wedge 34 in FIG. 3. For example, one or more segments of the second mating units 44 coupled to each of the top surfaces 38 in FIG. 3 may be releasably engaged with a set of the plurality of discrete attachment points 916 of the mating unit 904 to retain the wedge 34 on the sleeve portion 902 such that the peak 40 of the wedge 34 aligns with a back portion of a joint of a user's body.

Figures 11A, 11B:
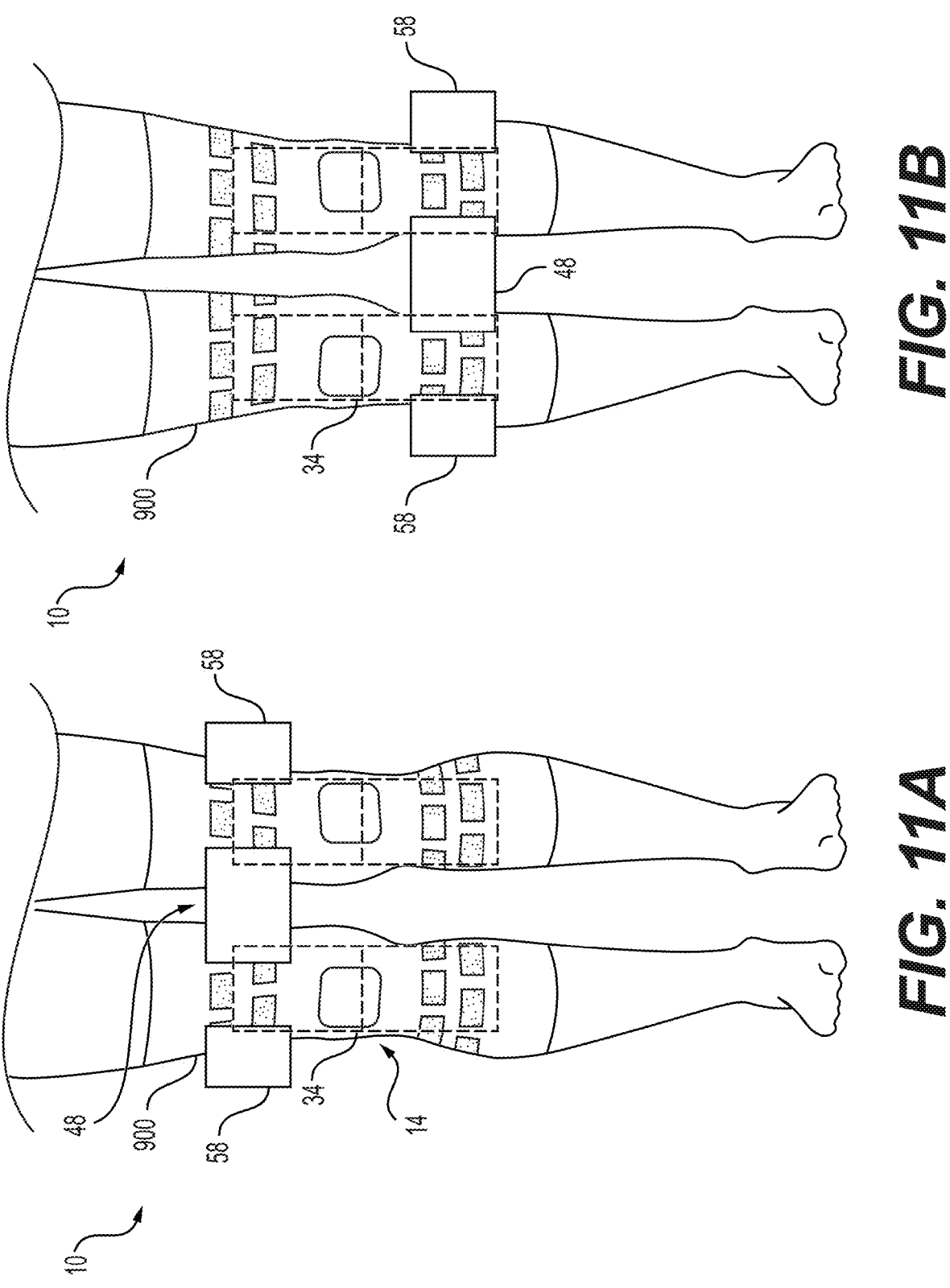
FIGS. 11A and 11B are front in-use view of the other brace of an embodiment of the disclosure.

To further illustrate the foregoing FIGS. 11A and 11B will now be described. FIGS. 11A and 11B provide an in-use view of the brace 900. As shown in FIGS. 11A and 11B, a pair of the braces 900 may each be worn around a respective one of the user's knees. The inner support 48 can be coupled between each of the braces 900 at an upper portion and lower portion of the user's legs, as shown in FIGS. 11A and 11B respectively. Additionally, a pair of the outer supports 58 may each be coupled to a respective one of the braces 900 at an upper portion and lower portion of the user's legs, as shown in FIGS. 11A and 11B respectively. In this way each of the user's knees are supported regardless of which side the user is lying on. A pair of the wedges 34 may each be coupled to a respective one of the braces 900 to support each of the user's knees when the user is lying on his or her back. As shown in FIGS. 11A and 11B, the inner support 48 and the outer support 58 can be aligned with each of the user's knees. Further, in FIGS. 11A and 11B, the wedge 34 is coupled to the brace 900 and the wedge 34 is positioned on the back side of the user's knees. Additionally, in FIG. 11, the inner support 48 is coupled to the brace 900 and the inner support 48 is positioned on the interior sides of the user's knees, and the outer support 58 is coupled to the brace 900 and the outer support 58 is positioned on the outer sides of the user's knees.

FIGS. 6-8, FIGS. 11A, and 11B show the modular support system being implemented with a user's knee. However, the modular support system may be implemented with any joint of a user's body, for example, elbows, ankles, shoulders, hip joints, fingers, toes, wrists, or any other desired joint. Additionally, the modular support system may be used by a user in several body positions, for example, lying, reclining, sitting, any other desired body position or combination thereof. Additionally, the modular support system may be used by a user in several anatomical positions, for example, prone, supine, right lateral recumbent, Fowler's, left lateral recumbent, Trendelenburg, any other desired anatomical position or combination thereof.

Further, in some embodiments, the sleeve portion 902 may be made from a combination of a microfiber polyester or any other material that is moisture wicking, lightweight, elastic, and/or absorbent. For example, the sleeve portion 902 may be made from one or more of the following materials: neoprene, polyester, cotton, nylon, spandex, or any other desired material. In some embodiments, the sleeve portion 902 may be designed to provide compression to keep a user's circulation flowing. More specifically, a pressure gradient produced by the sleeve portion 902 may manipulate the user's arteries and veins to increase circulatory efficiency. This may help to reduce swelling of one or more of the user's body parts.

In some embodiments, the plurality of discrete attachment points 916 of the mating unit 904 may comprise hook and loop fasteners or the like. As described, the mating unit 904 includes the discrete attachment points 916 that are coupled to the sleeve portion 902 rather than including contiguous strips coupled along the circumference of the sleeve portion 902. This allows the sleeve portion 902 to expand and contract to accommodate different sized patients and enable the sleeve portion 902 to be easily pulled up over a joint.

Moreover, in some embodiments, the sleeve portion 902 may include pockets for implementing cold therapy. For example, the pockets may be configured to hold ice or gel packs that allow placement of the ice or gel packs on or near portions of the user's body. This may help to reduce swelling for a user. In some embodiments, at least one side of a pocket may be perpetually coupled to the sleeve portion 902 (e.g., sewn to the sleeve portion 902) and the remaining sides of the pocket may be temporarily coupled via an attachment system (e.g., hook and loop fasteners). In some embodiments, all sides of the pocket may be temporarily coupled via an attachment system. For example, one or more pockets may be attached to the sleeve portion 902 in sections of the sleeve portion 902 near a user's joint.

Figure 12:
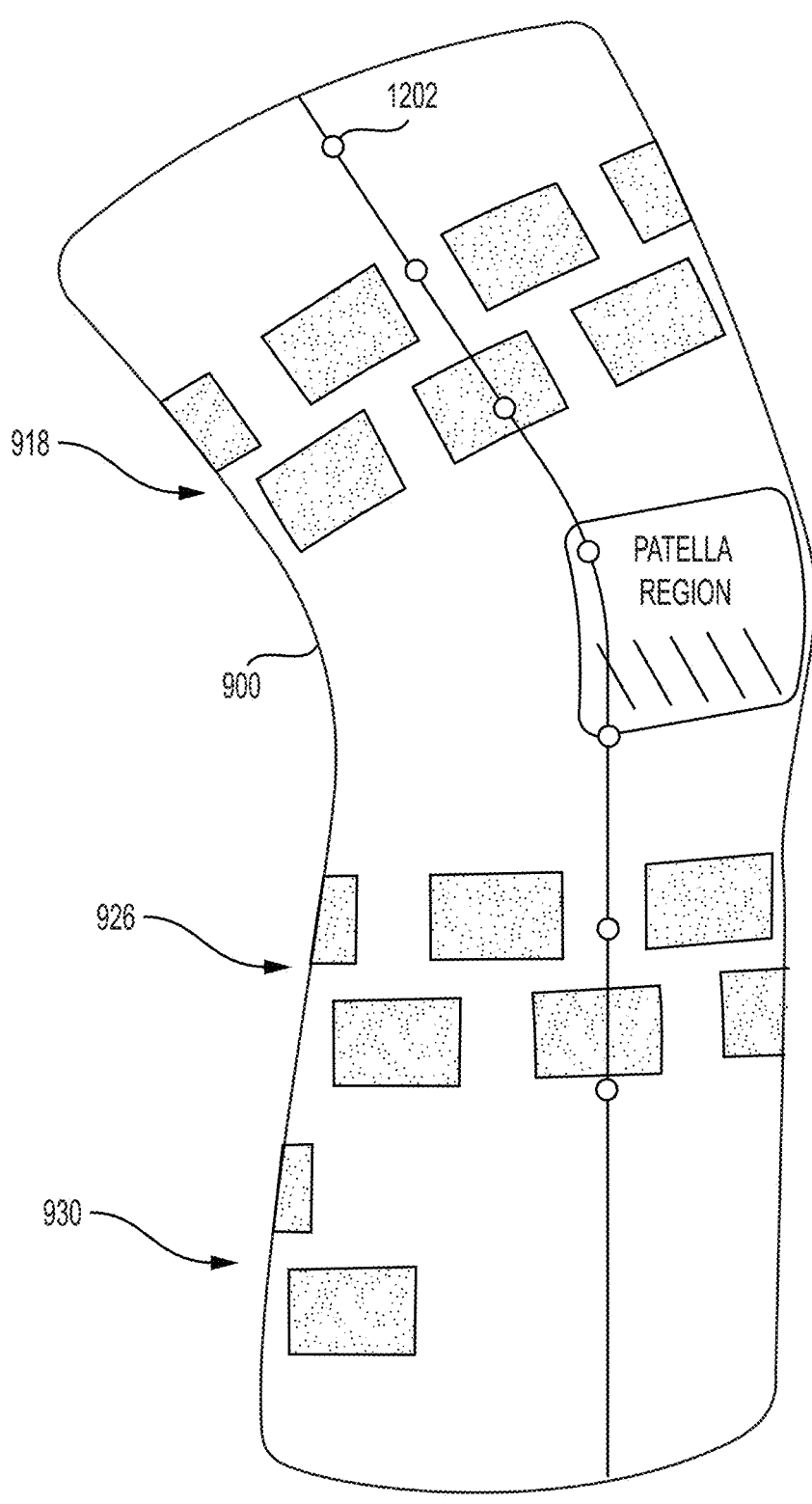
FIG. 12 is an exemplary embodiment of sensors coupled to the other brace of an embodiment of the disclosure.

The brace 900 may be configured to fit on any of the user's body parts, such as an arm, a wrist, a neck, a torso, a leg, a knee, an ankle, hips, or any other suitable body part. Still yet, in some embodiments, the brace 900 may include sensors. FIG. 12 illustrates an exemplary arrangement of sensors attached or connected to brace 900. For example, in FIG. 12, the brace 900 includes sensors 1202. The sensors 1202 may be configured to detect information associated with the user. For example, the sensors 1202 may detect a measured level of force exerted from the user, a temperature of the one or more body parts in contact with the user, a movement of the brace 900, any other suitable information, or any combination thereof.

In some embodiments, the sensors 1202 may be configured to measure angles of extension and/or bend of body parts and transmit the measured angles to a computing device of a user or a medical professional (e.g., a computer, a smartphone, a tablet, a smartwatch, etc.). The sensors 1202 may be included in the brace 900 that includes the one or more processing devices, memory devices, and/or network interface cards. In some embodiments, the sensors 1202 may be disposed in a cavity of the brace 900. The cavity of the brace 900 may be located near a portion of the brace 900 where the brace 900 bends and extends with the user's body. For example, the brace 900 may be configured to secure to a portion of the user's body (e.g., arm, leg, or any other desired portion) to measure angles of bend as the portion of the user's body is extended away from the body or retracted closer to the body.

Additionally, in some embodiments, the sensors 1202 may be configured to track a range of motion of a user. For example, the sensors 1202 may include gyroscope, a device used to measure and maintain orientation and angular velocity, to detect measurable motion. For example, after a user has anterior cruciate ligament (ACL) reconstruction, the sensors 1202 of the modular comfort system may be used to maintain the range of motion of a knee of the user between 0° to 30°. If the user moves beyond this range, an alarm may sound. The brace 900 could also be used for monitoring joint replacements. In some embodiments, the sensors 1202 may be configured for monitoring a temperature of a portion of the user's body covered by the sleeve portion 902.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

What is claimed is:

1. A modular support system, comprising:
   a brace comprising:
   a sleeve portion extending in a length direction between a first opening at a first end of the sleeve portion and a second opening at a second end of the sleeve portion, the first opening and the second opening adapted to enable a first portion of a user's body to pass through the sleeve portion and a second portion of the user's body to remain within the sleeve portion, the sleeve portion extending about the first and second openings in a circumferential direction; and
   a first mating unit comprising a plurality of discrete attachment points coupled to an outer surface of the sleeve portion, the discrete attachment points including a first set of the discrete attachment points and a second set of the discrete attachment points being spaced from one another in the length direction, wherein each of the first and second sets of the discrete attachment points are arranged as an array with a plurality of the discrete attachment points in a plurality of rows in the length direction, and a plurality of the discrete attachment points in the circumferential direction about the sleeve portion, and wherein the first and second sets of the discrete attachment points span around an entire circumference of the sleeve portion; and
   a wedge comprising:
   a second mating unit, wherein the second mating unit is adapted to couple with a set of the plurality of discrete attachment points to support one or more portions of the user's body.

2. The modular support system of claim 1, wherein the wedge further comprises an inner support comprising:
   a first lateral surface that is concavely arcuate configured to conform to a curvature of a portion of the user's body adjacent a joint; and
   a third mating unit coupled to the first lateral surface, wherein the third mating unit is removably coupled to the sleeve portion such that the inner support is positioned on the portion of the user's body at a medial side of the joint.

3. The modular support system of claim 2, wherein the wedge further comprises an outer support comprising:
   a second lateral surface that is concavely arcuate configured to conform to the curvature of the portion of the user's body adjacent the joint; and
   a fourth mating unit coupled to the second lateral surface, wherein the fourth mating unit is removably coupled to the sleeve portion such that the outer support is positioned on the portion of the user's body at a lateral side of the joint.

4. The modular support system of claim 3, wherein the fourth mating unit is adapted to couple with another set of the plurality of discrete attachment points to support the one or more portions of the user's body.

5. The modular support system of claim 2, wherein the third mating unit is adapted to couple with another set of the plurality of discrete attachment points to support the one or more portions of the user's body.

6. The modular support system of claim 2, wherein the inner support further comprises:

a second lateral surface that is concavely arcuate configured to conform to the curvature of the portion of the user's body adjacent another joint; and a fourth mating unit coupled to the second lateral surface, wherein the fourth mating unit is removably coupled to a sleeve portion of a second brace such that the inner support is positioned on the portion of the user's body at a medial side of the other joint.

7. The modular support system of claim 1, wherein the sleeve portion further defines an opening for at least a portion of a joint.

8. The modular support system of claim 7, wherein the first set of the plurality of discrete attachment points are coupled to the outer surface of the sleeve portion in a section of the sleeve portion adjacent a first side of the opening and the second set of the plurality of discrete attachment points are coupled to the outer surface of the sleeve portion in a section of the sleeve portion adjacent a second side of the opening, wherein the first side is opposite the second side.

9. The modular support system of claim 1, wherein the plurality of discrete attachment points of each of the first and second sets are substantially evenly spaced from one another in the circumferential direction.

10. The modular support system of claim 1, wherein each discrete attachment point in a first row of the plurality of rows of each of the first and second sets of discrete attachment points is substantially aligned with a corresponding discrete attachment point in a second row of the plurality of rows of each of the first and second sets of discrete attachment points.

11. The modular support system of claim 1, wherein each discrete attachment point in a first row of the plurality of rows of each of the first and second sets of discrete attachment points is substantially staggered from one or more discrete attachment points in a second row of the plurality of rows of each of the first and second sets of discrete attachment points.

12. The modular support system of claim 1, wherein the plurality of discrete attachment points are substantially shaped as: a circle, an oval, a triangle, a square, a rectangle, a hexagon, an octagon, a decagon, a semi-hexagon, a semi-octagon, a semi-decagon, or any combination thereof.

13. The modular support system of claim 1, wherein the wedge further comprises a first top surface, a second top surface, and a peak, the first top surface adjoining the second top surface to form the peak, and wherein the second mating unit is coupled to the first top surface and the second top surface and is adapted to couple with the set of the plurality of discrete attachment points such that the peak aligns with a back portion of a joint of the user's body.

14. The modular support system of claim 1, wherein the first and second sets of attachment points are spaced from one another by a joint region of the sleeve configured to overlie a joint of the user during use.

15. The modular support system of claim 1, wherein the first and second sets of the discrete attachment points include two rows of the attachment points.

16. A modular support system, comprising:

a brace comprising:

a sleeve portion extending in a length direction between a first opening at a first end of the sleeve portion and a second opening at a second end of the sleeve portion, the first opening and the second opening adapted to enable a first portion of a user's body to pass through the sleeve portion and a second portion of the user's body to remain within the sleeve portion;

a first mating unit comprising a plurality of discrete attachment points coupled to an outer surface of the sleeve portion, the discrete attachment points including a first set of the discrete attachment points, a second set of the discrete attachment points and a third set of discrete attachment points being spaced from one another in the length direction, wherein each of the first, second and third sets of the discrete attachment points are arranged as an array with a plurality of the discrete attachment points arranged in a plurality of rows in the length direction and a plurality of the discrete attachment points dispersed in a circumferential direction about the sleeve portion; and a wedge comprising:

a second mating unit, wherein the second mating unit is adapted to couple with a set of the plurality of discrete attachment points to support one or more portions of the user's body.

17. The modular support system of claim 16, wherein the first set of the plurality of discrete attachment points are coupled to the outer surface of the sleeve portion in a section of the sleeve portion adjacent a first side of the opening and the second set of the plurality of discrete attachment points are coupled to the outer surface of the sleeve portion in a section of the sleeve portion adjacent a second side of the opening, wherein the first side is opposite the second side.

18. The modular support system of claim 17, wherein the first and second sets of the discrete attachment points span around an entire circumference of the sleeve portion.

19. The modular support system of claim 16, wherein the first and second sets of the discrete attachment points span around an entire circumference of the sleeve portion.

20. A modular support system, comprising:

a brace comprising:

a sleeve portion extending in a length direction between a first opening at a first end of the sleeve portion and a second opening at a second end of the sleeve portion, the first opening and the second opening adapted to enable a first portion of a user's body to pass through the sleeve portion and a second portion of the user's body to remain within the sleeve portion, the sleeve portion extending about the first and second openings in a circumferential direction;

a first mating unit comprising a plurality of discrete attachment points coupled to an outer surface of the sleeve portion, the plurality of discrete attachment points includes a first set of the discrete attachment points and a second set of the discrete attachment points separated from one another in the length direction, wherein the discrete attachment points of each of the first and second sets are arranged in a plurality of rows and are substantially evenly spaced from each other in the circumferential direction;

wherein the sleeve portion defines a joint opening between the first and second sets of discrete attachment points for receiving a user's joint;

a wedge comprising:

a second mating unit, wherein the second mating unit is adapted to couple with a set of the plurality of discrete attachment points to support one or more portions of the user's body.

* * * * *